(12) United States Patent
Holme et al.

(10) Patent No.: US 8,858,918 B2
(45) Date of Patent: *Oct. 14, 2014

(54) CHEWING GUM AND CONFECTIONERY COMPOSITIONS WITH ENCAPSULATED STAIN REMOVING AGENT COMPOSITIONS, AND METHODS OF MAKING AND USING THE SAME

(75) Inventors: Samantha Katharine Holme, Pompton Plains, NJ (US); Shiuh John Luo, Livingston, NJ (US)

(73) Assignee: Intercontinental Great Brands LLC, East Hanover, NJ (US)

( * ) Notice: Subject to any disclaimer, the term of this patent is extended or adjusted under 35 U.S.C. 154(b) by 663 days.

This patent is subject to a terminal disclaimer.

(21) Appl. No.: 12/557,624

(22) Filed: Sep. 11, 2009

(65) Prior Publication Data

US 2010/0003310 A1 Jan. 7, 2010

Related U.S. Application Data

(60) Division of application No. 11/301,577, filed on Dec. 13, 2005, now abandoned, which is a continuation of application No. 10/292,139, filed on Nov. 12, 2002, now Pat. No. 7,041,277, which is a continuation-in-part of application No. 10/058,448, filed on Jan. 28, 2002, now Pat. No. 6,479,071, which is a continuation-in-part of application No. 09/947,876, filed on Sep. 6, 2001, now Pat. No. 6,485,739, which is a continuation-in-part of application No. 09/741,523, filed on Dec. 20, 2000, now Pat. No. 6,471,945.

(60) Provisional application No. 60/188,554, filed on Mar. 10, 2000.

(51) Int. Cl.
| | |
|---|---|
| A23G 4/00 | (2006.01) |
| A23G 4/06 | (2006.01) |
| A23G 4/08 | (2006.01) |
| A23G 4/02 | (2006.01) |
| A23G 3/36 | (2006.01) |
| A23L 1/00 | (2006.01) |
| A23G 4/20 | (2006.01) |
| A61Q 11/00 | (2006.01) |
| A61K 8/11 | (2006.01) |
| A61K 8/36 | (2006.01) |
| A23G 4/12 | (2006.01) |
| A23G 3/40 | (2006.01) |
| A23G 3/02 | (2006.01) |

(52) U.S. Cl.
CPC .. *A23G 4/20* (2013.01); *A23G 4/02* (2013.01); *A23G 4/066* (2013.01); *A23G 3/36* (2013.01); *A23L 1/0029* (2013.01); *A61Q 11/00* (2013.01); *A61K 8/11* (2013.01); *A61K 2800/412* (2013.01); *A61K 8/361* (2013.01); *A23G 4/064* (2013.01); *A23G 3/368* (2013.01); *A23G 3/362* (2013.01); *A23G 4/126* (2013.01); *A23G 4/00* (2013.01); *A23G 4/06* (2013.01); *A23G 3/40* (2013.01); *A23V 2002/00* (2013.01); *A23G 3/0205* (2013.01)
USPC ........... 424/48; 424/440; 424/49; 426/3; 426/5

(58) Field of Classification Search
USPC ................... 424/48, 49; 426/3, 5
See application file for complete search history.

(56) References Cited

U.S. PATENT DOCUMENTS

| | | | | |
|---|---|---|---|---|
| 4,238,475 | A | * | 12/1980 | Witzel et al. ............... 424/48 |
| 4,346,493 | A | * | 8/1982 | Goudsmit ............... 15/104.93 |
| 4,585,649 | A | | 4/1986 | Lynch |
| 4,933,190 | A | * | 6/1990 | Cherukuri et al. ............. 426/5 |
| 4,950,479 | A | | 8/1990 | Hill et al. |
| 4,952,407 | A | | 8/1990 | Record et al. |
| 5,057,309 | A | | 10/1991 | Hill et al. |
| 5,139,794 | A | | 8/1992 | Patel et al. |
| 5,380,530 | A | * | 1/1995 | Hill ............................ 424/440 |
| 5,629,036 | A | | 5/1997 | Yanetani et al. |
| 5,736,175 | A | | 4/1998 | Cea et al. |
| 5,756,074 | A | | 5/1998 | Ascione et al. |
| 5,824,291 | A | | 10/1998 | Howard |
| 6,013,274 | A | * | 1/2000 | Chaykin ...................... 424/440 |
| 6,344,222 | B1 | * | 2/2002 | Cherukuri et al. ............. 426/6 |
| 6,616,915 | B1 | | 9/2003 | Griesbach et al. |
| 7,041,277 | B2 | | 5/2006 | Holme et al. |
| 2001/0008643 | A1 | | 7/2001 | Schulz et al. |
| 2002/0098157 | A1 | | 7/2002 | Holme et al. |
| 2002/0159955 | A1 | | 10/2002 | Luo et al. |
| 2003/0124064 | A1 | | 7/2003 | Luo et al. |

FOREIGN PATENT DOCUMENTS

| | | |
|---|---|---|
| EP | 0252374 A1 | 1/1988 |
| WO | 8800463 A1 | 1/1988 |
| WO | 9619193 A1 | 6/1996 |
| WO | 9823165 A1 | 6/1998 |
| WO | WO 99/44436 * | 9/1999 |

OTHER PUBLICATIONS

"Causes of teeth staining", internet citation retrieved on May 15, 2012, http://www.startsmiling.com/Teeth-Staining.aspx.

\* cited by examiner

*Primary Examiner* — Lezah Roberts
(74) *Attorney, Agent, or Firm* — Hoffmann & Baron, LLP

(57) ABSTRACT

A composition in the form of a chewing gum composition or a confectionery composition containing an encapsulated stain removing agent selected from anionic and non-ionic surfactants and methods of preparing and using the same to remove stains from dental material including teeth.

19 Claims, No Drawings

CHEWING GUM AND CONFECTIONERY COMPOSITIONS WITH ENCAPSULATED STAIN REMOVING AGENT COMPOSITIONS, AND METHODS OF MAKING AND USING THE SAME

RELATED APPLICATIONS

This application is a divisional application of U.S. application Ser. No. 11/301,577, filed Dec. 13, 2005, which is a continuation of U.S. application Ser. No. 10/292,139, filed Nov. 12, 2002, which is a continuation-in-part of U.S. application Ser. No. 10/058,448, filed Jan. 28, 2002, now U.S. Pat. No. 6,479,071, issued on Nov. 12, 2002, which is a continuation-in-part of U.S. application Ser. No. 09/947,876, filed Sep. 6, 2001, now U.S. Pat. No. 6,485,739, issued on Nov. 26, 2002, which is a continuation-in-part of U.S. application Ser. No. 09/741,523, filed Dec. 20, 2000, now U.S. Pat. No. 6,471, 945, issued on Oct. 29, 2002, which claims the benefit of U.S. Provisional Application No. 60/188,554, filed Mar. 10, 2000.

FIELD OF THE INVENTION

The present invention is generally directed to chewing gum and confectionery compositions containing an effective amount of an encapsulated stain removing component selected from anionic and non-ionic surfactants and to processes of making the compositions in a manner which facilitates the release of the stain removing component.

BACKGROUND OF THE INVENTION

Tooth whitening or stain removing components are known to be added to dentifrice compositions such as toothpastes, mouthwashes, and the like. Such compositions include dicalcium phosphates, peroxides, percarbonates and the like such as disclosed in, for example, U.S. Pat. Nos. 5,256,402; and 5,824,291.

The employment of surfactants including non-ionic surfactants is known for laundry detergent compositions. Such surfactants are disclosed, for example, in International Publication Nos. WO 92/06160 and WO 95/33034. The use of non-ionic surfactants in laundry detergent compositions is known to improve the effectiveness of such compositions against greasy/oily stains.

U.S. Pat. No. 5,645,821 discloses an oral hygiene composition to clean and whiten teeth which includes water, gelling agent, anionic surfactant and a mixture of alkaline earth metal hydroxides and carbonates. WO 88/00463 discloses an oral composition for removing and/or preventing plaque and for removing stains which includes an oily compatible surfactant and at least one weight percent of a benzoic acid salt. The composition is also stated to contain a biocide such as chlorhexidine or derivative thereof. An exemplified surfactant is sodium lauryl sulfate and the composition is also stated to contain plasticizers including polyethylene glycol, glycerin and the like. The reference states that the composition may be used in the form of dentifrices, lozenges or chewing gum.

Other chewing gum compositions and the active ingredient for removing stains disclosed therein include WO 99/43294 (chlorite ion); WO 99/27798 (a water-soluble product including sodium bicarbonate and encapsulated aspartame); Chinese Patent Document No. 1196235 (hydrogen peroxide); U.S. Pat. No. 5,824,291 (alkaline metal carbonate peroxyhydrates); WO 98/29088 (cysteine proteinase); WO 98/18339 (bone minerals, calcium triphosphate and/or hydroxyapatite); and U.S. Pat. No. 5,629,035 (alkaline metal bicarbonates).

U.S. Pat. No. 4,952,407 discloses a gum composition containing a dental plaque removing agent in the form of glycerol monolaurate. The composition typically includes a high filler content wherein the filler is an inorganic material such as calcium carbonate, talc, sodium bicarbonate dicalcium phosphate and mixtures thereof.

For coated chewing gum compositions, it is known to provide an active agent such as a medicament in the chewing gum coating and optionally in the core such as disclosed in WO 00/35296 and WO 00/35298.

U.S. patent application Ser. No. 09/741,523 filed Dec. 20, 2000 of the Assignee herein covers a chewing gum and confectionery composition containing an anionic and/or non-ionic surfactant (e.g. sodium stearate) which may be present in the core, a coating including a centerfill product.

Delivery systems for the delivery of various components of a chewing gum composition including encapsulation systems are disclosed in U.S. Pat. Nos. 4,569,852; 4,695,463; 4,981, 698; 5,004,595; 5,266,335; and 5,679,389, as well as International Publication Nos. WO 98/23165; WO 00/35295; and WO 00/35298. Encapsulation systems for surfactant containing products are disclosed in U.S. Pat. Nos. 4,473,485; 4,597, 885; and 5,385,737.

Unlike toothpaste, mouthwash and other dentifrice compositions, gum compositions present unique problems in delivering agents. Chewing gum compositions typically comprise a water-insoluble gum base which provides the bulk to the gum composition but which invariably traps agents having compatibility with the gum base. Adding additional amounts of an agent is problematical because the same can have an adverse effect on the integrity, sensory and/or taste properties of the gum composition.

It would therefore be a significant advance in the art of providing a stain removing agent for the cleaning of dental material including teeth if such stain removing agent could be effectively incorporated into a chewing gum composition and released therefrom during the chewing process in a manner which provides an effective amount of the stain removing agent. The chewing gum composition would then not only provide chewing satisfaction to the user, but would also provide a beneficial dental effect.

Confectionery compositions are well known in the art. Such compositions include, for example, hard boiled candies, nougats, panning goods, gel confections, centerfill confections, fondants, and the like. Unlike chewing gum compositions which often remain in the mouth for several minutes and often quite longer, confectionery compositions tend to have a short life in the mouth because they dissolve relatively quickly upon chewing. Nonetheless, it would be of great benefit to provide confectionery compositions with an effective amount of a stain removing agent to provide such products to render them capable of providing a beneficial dental effect.

SUMMARY OF THE INVENTION

The present invention is generally directed to stain-removing chewing gum and confectionery compositions in which a stain removing material has been effectively incorporated therein so that a sufficient amount is available for a stain removing effect.

In a particular aspect of the present invention, there is provided a stain-removing composition selected from a chewing gum composition and a confectionery composition comprising a stain removing effective amount of at least one stain removing agent selected from the group consisting of anionic and non-ionic surfactants, in which the stain removing agent has been encapsulated to enable an effective amount of the stain removing agent to be released from the composition.

In accordance with one aspect of the present invention, there is provided a stain-removing chewing gum composition comprising a core and a coating comprised of at least one layer with at least one of the core and coating comprising a stain removing effective amount of at least one stain removing agent selected from the group consisting of anionic and non-ionic surfactants and mixtures thereof in an encapsulated form such as a granule. A method of removing stains by employing the chewing gum composition of the present invention is also disclosed.

In a further aspect of the present invention there is provided a stain removing confectionery composition comprising a stain removing effective amount of at least one stain removing agent selected from the group consisting of anionic and non-ionic surfactants and mixtures thereof in an encapsulated form such as a granule. A method of removing stains by employing the confectionery compositions of the present invention is also disclosed.

In a preferred form of the invention, the surfactants for both the gum and confectionery compositions are selected from the group consisting of medium and long chain fatty acid esters and salts, most preferably containing 14-20 carbon atoms, and especially sodium stearate and sodium palmitate and mixtures thereof, as well as a mixture of citric acid esters of mono and diglycerides.

In a further preferred form of the invention, the active stain removing agent is encapsulated in a manner such as described in H. Menzi et al., U.S. Pat. No. 6,056,949, the entire content of which is incorporated herein by reference. Not only does encapsulation provide enhanced delivery of the stain-removing agent to dental surfaces but it also tends to mask the taste of the stain-removing agent which is a particular advantage when relatively large amounts of the stain-removing agent are used.

DETAILED DESCRIPTION OF THE INVENTION

From prior pending Application U.S. Ser. No. 09/741,523 filed Dec. 20, 2000, applicants determined that an effective stain removing chewing gum and confectionery compositions can be prepared by a suitable selection of stain-removing agents and the formulation of the gum and confectionery compositions and the manner in which the stain-removing agents are added to the compositions which enables the release of the stain-removing agent in an effective amount so that it may come into contact with dental surfaces including tooth surfaces while maintaining the organoleptic properties commonly associated with such products.

Applicants have discovered that encapsulating the active stain-removing agents achieves additional benefits including, but not limited to, reducing the rate at which the stain-removing gum composition is retained in the gum bolus and enabling more of the stain-removing agent to be effectively released from the compositions to provide an improved stain-removing effect.

More specifically, the stain-removing agents employed in the present invention tend to solubilize the hydrophobic gum base which can adversely affect the organoleptic properties of a chewing gum composition. This problem may be overcome by increasing the amount of gum base used in the chewing gum composition and/or adding fillers (e.g. atomite). While this method is satisfactory in maintaining the organoleptic properties of the gum composition, it has been observed that the gum base formulation is more difficult to process.

The present invention overcomes the problem by encapsulating the stain-removing agent in a hydrophilic material which does not readily solubilize the hydrophobic gum base. Accordingly, when the gum composition is chewed the encapsulated stain-removing agent is readily released form the bolus without solubilizing the gum base. The encapsulated product, typically in the form of granules, is released into the oral cavity where the encapsulating material dissolves when contacted by saliva. An effective increase in the amount of stain-removing agent for removing stains from dental surfaces is thereby achieved.

The chewing gum compositions of the present invention, may be coated or uncoated and be in the form or slabs, sticks, pellets, balls and the like. The composition of the different forms of the chewing gum compositions will be similar but may vary with regard to the ratio of the ingredients. For example, coated gum compositions may contain a lower percentage of softeners. Pellets and balls have a small chewing gum core, which is then coated with either a sugar solution or a sugarless solution to create a hard shell. Slabs and sticks are usually formulated to be softer in texture than the chewing gum core. It may be preferred to formulate a slab or stick gum having a firmer texture (i.e. with less softener than is typically employed) in order to reduce even further the ability of the active surfactant to solubilize the gum base.

Centerfilled gum is another common gum form. The gum portion has a similar composition and mode of manufacture to that described above. However, the centerfill is typically an aqueous solution or gel, which is injected into the center of the gum during processing. The stain removing agent could optionally be incorporated into the centerfill during manufacture of the fill or into the chewing gum. The centerfill gum may also be optionally coated and may be prepared in various forms such as in the form of a lollipop.

For practice of the present invention it is preferred to use a coated gum wherein the stain removing agent is in at least one of the core and the coating. Most preferred for removing stains is a coated gum wherein the stain removing agent is at least in the coating.

The chewing gum composition of the present invention includes gum base and most of the other typical chewing gum composition components such as sweeteners, softeners, flavorants and the like. At least one stain removing agent is employed in the present invention which is selected from anionic and non-ionic surfactant and which is encapsulated as described hereinafter. The chewing gum composition may contain a reduced amount of softening agents such as lecithin or glycerin or may eliminate softeners. In addition, the chewing gum composition may contain a larger amount of sugar alcohols than conventional chewing gum compositions to facilitate delivery of the stain removing agent employed in the present invention to the tooth surfaces.

The active stain-removing agents are encapsulated in a hydrophilic encapsulating material. Such materials are typically used for the manufacture of flavorant or odorant granulates and generally have a particle size of from about 0.02 to 3.0 mm, more commonly from about 0.1 to 1.5 mm diameter. Examples of such materials include carbohydrates including, starches, dextran, sugars such as sucrose, glucose, lactose and sugar alcohols, such as maltitol and sorbitol, gums such as gum arabic, carrageenan, locust bean gum, acacia gum, and tragacanth, cellulosic materials such as carboxymethylcellulose, hydroxymethyl cellulose, proteins, wheat protein, water soluble polymers and mixtures thereof and the like. Examples of water soluble polymers include ethylene acrylic acid polymers, polyvinyl alcohol block polymers, starch loaded polyethylene polymers, polylactates, starch based polymers, methyl methacrylate polymers, ethyl methacrylate polymers, copolymers of ethylene and carbon monoxide, hydroxypropylated starch (70% amylose), methylcellulose, ethylcellulose, cellulose diacetate, modified natural polymers, extruded potato starch, caprolactone polyester, acrylamide block polymers, ethylene oxide polymers, poly (acrylonitrile) polymers, poly (acrylamide) polymers and mixtures thereof.

The term "water-soluble polymer" means that the polymer has sufficient water solubility to enable delivery of the stain removing agent to the oral cavity in manner sufficient to provide a desirable stain removing effect.

The amount of the encapsulating material will typically be in the range of from about 20 to 40% by weight based on the total weight of the encapsulated active stain-removing agent. The preferred amount of the encapsulating material is from about 25 to 35% by weight. It will be understood that greater or less amounts of the encapsulating material may be used depending in part of the type of gum or confectionery composition and which stain-removing agent is employed. Furthermore, it is generally desirable to have as high a load of the stain-removing agent as feasible in order to maximize the stain removing potential of the composition.

In accordance with one aspect of the chewing gum composition of the present invention, the encapsulated stain removing agent is added during the manufacture of the chewing gum composition, that is, with the sweeteners, flavorants and the like. In a preferred aspect of the present invention, the encapsulated stain removing agent is added as one of the last steps, preferably the last step in the formation of the chewing gum composition in order to protect the encapsulated material. Thus, the encapsulated stain removing agent while only loosely contained within the gum composition can be more effectively released therefrom during a typical chewing operation.

The insoluble gum base generally comprises elastomers, elastomer plasticizers, waxes, fats, oils, emulsifiers, fillers, texturizers and may include the encapsulated stain-removing agent as hereinafter described.

Elastomers constitute from about 5 to 95% by weight of the base, preferably 10 to 70% by weight and most preferably 15 to 45% by weight. Examples of elastomers includes synthetic elastomers such as polyisobutylene, polybutylene, isobutylene-isoprene co-polymers, styrene-butadiene co-polymers, polyvinylacetate and the like. Elastomers may also include natural elastomers such as natural rubber as well as natural gums such as jelutong, lechi caspi, perillo, massaranduba balata, chicle, gutta hang kang or mixtures thereof. Other elastomers are known to those of ordinary skill in the art.

Elastomer plasticizers modify the finished gum firmness this when used in the gum base. Elastomer plasticizers are typically present in an amount of from about 0 to 75% by weight of the gum base, preferably from about 5 to 45% by weight and most preferably from about 10 to 30% by weight. Examples of elastomer plasticizers include natural rosin esters such as glycerol ester of partially hydrogenated rosin, glycerol ester of tall oil rosin, pentaerythritol esters of partially hydrogenated rosin, methyl and partially hydrogenated methyl esters of rosin, and the like. Synthetic elastomer plasticizers such as terpene resins may also be employed in gum base composition Waxes include synthetic and naturally occurring waxes such as polyethylene, bees wax, carnauba and the like. Petroleum waxes such a paraffin may also be used. The waxes may be present in the amount of from about 0 to 30% by weight of the gum base. Waxes aid in the curing of the finished gum and help improve the release of flavor and may extend the shelf life of the product.

Fillers modify the texture of the gum base and aid processing. Examples of such fillers include magnesium and aluminum silicates, clay, alumina, talc, titanium oxide, cellulose polymers, and the like. Fillers are typically present in an amount of from 1 to 60% by weight.

Examples of softeners used in gum base include hydrogenated and partially hydrogenated vegetable oils, cocoa butter, glycerol monostearate, glycerol triacetate, di and tri glycerides, fatty acids such as stearic acid, palmitic acid, oleic acid, linoleic acid, linolenic acid and the like.

The gum base constitutes between 5 and 95% by weight of the chewing gum composition, more typically 10 to 50% by weight, and most preferably 25 to 35% by weight of the chewing gum. A higher amount of gum base is preferred.

Other ingredients used in chewing gum compositions include sweeteners, both natural and artificial and both sugar and sugarless. Sweeteners are typically present in the chewing gum compositions in amounts of from about 20 to 80% by weight, preferably from about 30 to 60% by weight. Sugarless sweeteners include, but are not limited sugar alcohols such as sorbitol, mannitol, xylitol, hydrogenated starch hydrolysates, maltitol and the like may also be present. High intensity sweeteners such as sucralose, aspartame, salts of acesulfame, and the like. High intensity sweeteners are typically present from about 0 to 1.0% by weight.

Flavoring agents which can vary over a wide range may be selected in amounts from about 0.1 to 10.0% by weight, preferably from about 0.5 to 5.0% by weight. Flavoring agents for use in chewing gum compositions are well known and include citrus oils, peppermint oil, spearmint oil, oil of wintergreen, menthol and the like.

Softeners may be present to modify the texture of the chewing gum composition. Unlike typical gum compositions, softeners in the compositions of the present invention are typically present in reduced amounts of from about 0.5 to 10% by weight based on the total weight of the chewing gum.

Other materials which may be present in the gum composition of the present invention include antioxidants (e.g. butylated hydroxyanisole, butylated hydroxytoluene, beta-carotenes, tocopherols, colorants, flavorants and the like.

The encapsulated active stain-removing agent may be prepared by any known process for encapsulating materials including spray drying, employing fluidized bed—employing systems, or agglomeration.

Suitable encapsulation materials include, but are not limited to cellulose materials, such as ethyl cellulose, methylcellulose, hydroxyethyl cellulose and carboxymethyl cellulose, and the like, dextrin, maltodextrin, dextran, xanthin, modified starches, acacia, polydextrose, guar gum, pectin, locust bean gum, carrageenan, gum Arabic, tragacanth, baraya, ghatto, agar, alginates, fucellar, psyllium, sugar alcohols such as sorbitol, manitol, maltitol, xylitol and the like, proteins such as casein, gelatin, egg albumin whey and the like, and mixtures thereof.

A preferred method of preparing the encapsulated stain-removing agent is similar to that described in H. Menzi et al., U.S. Pat. No. 6,056,949. In such a process a solution which contains the encapsulating material is sprayed onto a core which may contain in whole or in part, the active ingredient, and then treated with a fluidized bed rotor-granulator.

The core may also contain a carrier for the active ingredient such as, for example, starches, sugars and like conventional carrier materials. The solution which may include a solvent such as water or a mixture of water and ethanol, is sprayed in the fluidized bed below the surface of the core material. The encapsulating material may be sugar based or sugar free. Preferred encapsulating materials are selected from mannitol, maltitol, gum arabic, carboxymethyl cellulose, egg protein and mixtures thereof. Suitable temperatures for the encapsulation process are from about 30 to 80° C., preferably from about 40 to 70° C.

The resulting particles may optionally be coated after the granulation process such as by spraying a solution, emulsion or a melt of a substance which is known to be suitable for this purpose such as fat, modified cellulose, gelatin plant or animal extract, gums such as gum arabic, starches including degraded starch or chemically modified starch as well as suitable synthetic materials such as polyvinyl pyrrolidone, polyethylene glycol and the like.

The particle size distribution of the encapsulated stain-removing agent is preferably kept within a narrow range which can be achieved by combining the effects of a) particle size of the encapsulating material, the composition of the emulsion, the spray rate of the emulsion, the structure of the rotating base plate of the granulator, the rate of rotation of the base plate, the air inlet velocity, the air temperature, such parameters being within the knowledge of those skilled in the art and exemplified in U.S. Pat. No. 6,056,949. For example, the spray rate of the emulsion is desirably within the range of from about 30 to 80 g/min.

Referring to the production of chewing gum compositions in accordance with the present invention, coating techniques for applying a coating for a chewing gum composition such as pan and spray coating are well known. Preferred in the practice of the present invention is coating with solutions adapted to build a hard candy layer. Both sugar and sugar alcohols may be used for this purpose together with high intensity sweeteners, colorants, flavorants and binders. When the encapsulated stain removing agent is provided in the coating of a chewing gum composition, the encapsulated stain removing agent is preferably, alternately, applied with the flavorant, most preferably with the encapsulated product being positioned in or about the middle of this coating.

The sweetener may be present in an amount of from about 30% to about 80% by weight of the coating syrup. The binder may be present in an amount of from about 1% to about 15% by weight of the coating syrup. Minor amounts of the optional additives may also be present. The sweeteners suitable for use in the coating syrup comprise sugarless sweeteners such as the polyhydric alcohols, e.g., xylitol, sorbitol, mannitol, and mixtures, thereof; as well as maltitol, isomaltitol, hydrogenated starch hydrolysates, and hydrogenated glucose syrups. Mono, di- and polysaccharide may also be included. For example, sugars such as sucrose, fructose, glucose, galatose and maltose may also be employed as a sweetener. Other sweeteners suitable for use in the coating syrup include, but are not limited to free saccharin acid, water soluble salts of saccharin, cyclamate salts, palatinit dihydrochalcones, glycyrrhizin, L-aspartyl-L-phenylalanine methyl ester, amino acid based sweeteners, talin, steviosides, dihydrochalcone compounds, acesulfame salts and mixtures thereof.

Other components may be added in minor amounts to the coating syrup and include moisture absorbing compounds, anti-adherent compounds, dispersing agents and film forming agents. The moisture absorbing compounds suitable for use in the coating syrups include mannitol or dicalcium phosphate. Examples of useful anti-adherent compounds, which may also function as a filler, include talc, magnesium trisilicate and calcium carbonate. These ingredients may be employed in amounts of about 0.5% to about 5% by weight of the syrup. Examples of dispersing agents which may be employed in the coating syrup include titanium dioxide, talc or other anti-adherent compounds as set forth above.

The coating syrup is usually heated and a portion thereof deposited on the cores. Usually a single deposition of the coating syrup is not sufficient to provide the desired amount or thickness of coating and it usually will be necessary to apply second, third or more coats of the coating syrup in order to build up the weight and thickness of the coating to desired levels with layers allowed to dry in-between coats.

A preferred aspect of the chewing gum composition invention adds an encapsulated stain removing agent to the coat. The encapsulated stain removing agent is preferably applied subsequent to the syrup coating. It is preferred to then apply a coat of high intensity sweetener prior to coating with the encapsulated stain removing agent. Application of the encapsulated stain removing agent is preferably done alternatively to application of a flavorant solution. In the practice of the present invention the encapsulated stain removing agent may be applied as a solution or may be applied as a dry charge. In coating a chewing gum composition, the applications of coating syrup are continued until the average gum piece weight reaches the required coating weight, preferably until the coat comprises 20-30% by weight of the final pellet weight.

The present invention also encompasses confectionery compositions containing a suitable selection of stain-removing agents. Confectionery compositions include compressed tablets such as mints, hard boiled candies, nougats, gels, centerfill confections, fondants, panning goods and other compositions falling within the generally accepted definition of confectionery compositions.

Confectionery compositions in the form of pressed tablets such as mints may generally be made by combining finely sifted sugar or sugar substitute, flavoring agent (e.g. peppermint flavor) bulking agent such as gum arabic, and an optional coloring agent. The flavoring agent, bulking agent are combined and then gradually the sugar or sugar substitute are added along with a coloring agent if needed.

The product is then granulated by passing through a seive of desired mesh size (e.g. 12 mesh) and then dried at typically 55 to 60° C. The resulting powder is fed into a tableting machine fitted with a large size punch and the resulting pellets are broken into granules and then pressed.

High boiled candies typically contain sugar or sugar substitute, glucose, water, flavoring agent and optional coloring agent. The sugar is dissolved in the water and glucose is then added. The mixture is brought to a boil. The resulting liquid to which may previously have been added a coloring agent is poured onto an oiled slab and cooled. The flavoring agent are then added and kneaded into the cooled mass. The resulting mixture is then fed to a drop roller assembly known in the art to form the final hard candy shape.

A nougat composition typically includes two principal components, a high boiled candy and a frappe. By way of example, egg albumen or substitute thereof is combined with water and whisked to form a light foam. Sugar and glucose are added to water and boiled typically at about 130-140° C. and the resulting boiled product is poured into a mixing machine and beat until creamy.

The beaten albumen and flavoring agent are combined with the creamy product and the combination is thereafter thoroughly mixed.

Further details regarding the preparation of confectionery compositions can be found in Skuse's Complete Confectioner (13$^{th}$ Edition) (1957) including pp. 41-71, 133-144, and 255-262; and Sugar Confectionery Manufacture (2$^{nd}$ Edition) (1995), E. B. Jackson, Editor, pp. 129-168, 169-188, 189-216, 218-234, and 236-258 each of which is incorporated herein by reference.

In accordance with the present invention, a stain-removing effective amount of an anionic and/or non-ionic surfactant is employed as a stain-removing agent for chewing gum and confectionery compositions which agent is encapsulated as described previously. Typical examples of the stain removing agents which may be employed in the present invention include sulfated butyl oleate, medium and long chain fatty acid esters and salts in particular the sodium and potassium salts of the stearate and palmitate, and methyl and ethyl esters thereof, sodium oleate, salts of fumaric acid, potassium glomate, organic acid esters of mono and diglycerides such as stearyl monoglyceridyl citrate, succistearin, dioctyl sodium sulfosuccinate, glycerol tristearate, lecithin, hydroxylated lecithin, sodium lauryl sulfate, acetylated monoglycerides, succinylated monoglycerides, monoglyceride citrate, ethoxylated mono- and diglycerides, sorbitan monostearate, calcium stearyl-2-lactylate, sodium stearyl lactylate, lactylated fatty acid esters of glycerol and propylene glycerol, glycerol-lactoesters of C8-C24 fatty acids, preferably glycerol-lactoesters of C14-C20 fatty acids, polyglycerol esters of C8-C24 fatty acids, preferably polyglycerol esters of C14-C20 fatty acids, propylene glycol alginate, sucrose C8-C24 fatty acid esters, preferably sucrose C14-C20 fatty acid esters, diacetyl tartaric or citric or lactic acid esters of mono and diglycerides, triacetin and the like and mixtures thereof.

Exemplary preferred stain removing agents are selected from sodium stearate and sodium palmitate and mixtures thereof, sodium oleate, a mixture of citric acid esters or lactic acid esters of monoglycerides and diglyercides, as for example, glycerol stearate, glycerol laurate and mixtures thereof, sucrose monostearate, sucrose distearate, sucrose monolaurate, sucrose dilaurate, polyglycerol esters of monostearate, polyglycerol esters of monolaurate and mixtures thereof.

The preferred surfactants for use in chewing gum compositions of the present invention are sodium stearate, usually available as an approximate 50/50 mixture with sodium palmitate, and, a mixture of at least one citric acid ester of mono and/or diglycerides. A suitable example of a commercial stain removing agent in the latter class is IMWITOR 370® sold by Condea Vista Company. A further preferred surfactant is a mixture of lactic acid esters of monoglycerides and diglycerides.

The amount of the stain-removing agent for chewing gum compositions is typically from about 0.2 to 2.0% by weight based on the total weight of the chewing gum composition and from about 60 to 80%, preferably 65 to 75% by weight of the encapsulated product. The preferred amount of the stain-removing agent is from about 0.4 to 1.2% by weight. The amount of the stain removing agent will vary depending upon the particular individual or combination of stain-removing agents employed, the type of other components of the chewing gum composition and their respective amounts. For example, a preferred amount of sodium stearate is about 0.5% by weight, a preferred amount of a mixture of lactic acid esters of monoglycerides and diglycerides is about 0.6% by weight while a preferred amount of a mixture of citric acid esters of mono- and diglycerides (IMWITOR 370®) is from about 0.6 to 1% by weight.

The preferred stain removing agents for use in the confectionery compositions of the present invention are sodium stearate, sodium palmitate and mixtures thereof. As indicated in connection with the chewing gum compositions, sodium stearate is usually available as an approximately evenly divided mixture with sodium palmitate.

The amount of the stain removing agent which may be employed in the confectionery compositions of the present invention will vary over a range depending on, for example, the type of confectionery composition and the particular individual or combination of stain removing agents which are employed. Generally, the amount of stain removing agent used in the confectionery compositions of the present invention will exceed the amount of the stain removing agent employed for the chewing gum composition for a particular stain removing agent.

Typically, the stain removing agent for confectionery compositions will be present in an amount of from about 0.2 to 20% by weight based on the total weight of the confectionery composition. The preferred amount of the stain removing agent is from about 3 to 17% by weight. The amount of the stain-removing agent employed in the encapsulated product is the same as that described above for the gum composition (e.g. generally from about 60 to 80% by weight). The relatively large amounts of the stain-removing agent in confectionery compositions of the present invention may affect the taste of the final product. However, it has been found that when such large amounts of the stain removing agent are encapsulated, there is a significant taste masking effect resulting therefrom which effectively eliminates or at least minimizes the taste concerns associated with the stain-removing agent.

EXAMPLES

The following examples are submitted for illustrative purposes only and are not intended to limit the scope of the application as fully covered by the specification and claims.

Example 1

Preparation of Gum Products with Encapsulated Stain-Removing Agent

A. Slab Gums

TABLE 1

| Ingredient | Sample 1 | Sample 2 |
|---|---|---|
| Gum base | 29.0000 | 29.0000 |
| Atomite (Filler) | 10.0000 | 10.0000 |
| Sorbitol | 35.1920 | 35.1920 |
| Mannitol | 13.5000 | 13.5000 |
| Glycerin | 8.0000 | 8.0000 |
| High Intensity sweetener* | 1.1640 | 1.1640 |
| Flavor | 1.9900 | 1.9900 |
| Sodium stearate** | 1.0000 | — |
| Enhance Power | 0.1540 | 0.1540 |
| IMWITOR370 ®*** | — | 1.0000 |
| Totals | 100.0000 | 100.0000 |

*Aspartame, Ace K mixtures
**Sodium stearate/sodium palmitate @ 50/50 encapsulated in granular form which is 75% by weight sodium stearate.
***IMWITOR 370 ® in an encapsulated granular form which is 75% by weight IMWITOR 370 ®

Samples 1 and 2 of the chewing gum compositions identified in Table 1 were prepared by conventional methods. The gum base was heated to sufficiently soften the base (e.g. about 80° C.) without adversely affecting the physical and chemical make up of the base. The molten gum base and the filler were then added to a mixing kettle. The sugar alcohols, glycerin, flavor, high intensity sweetener and stain removing agent were added with mixing to obtain a homogenous mixture.

An encapsulated stain-removing agent containing product was prepared in a similar to that described in U.S. Pat. No. 6,056,949. A solution containing the encapsulating material (e.g. mannitol) was sprayed onto sodium stearate in a fluidized bed rotor-granulator in the optional presence of a carrier material (e.g. a starch) to form encapsulated granules.

The encapsulated granules were added to the gum base composition. The mixture was then discharged from the mixing kettle and rolled and scored into a desired piece size by conventional techniques.

B. Coated Gums—Encapsulated Stain Removing Agent in Coat

TABLE 2

| Ingredient | Sample 3 | Sample 4 |
|---|---|---|
| Core Gum | | |
| Gum Base | 26.2500 | 26.2500 |
| Atomite (Filler) | 3.7500 | 3.7500 |
| Sorbitol | 33.3583 | 33.1917 |
| Mannitol | 7.5000 | 7.5000 |
| Flavorant | 2.8075 | 2.8075 |
| Glycerin | 1.0000 | 1.0000 |
| High Intensity Sweetener* | 0.7875 | 0.7875 |
| Coat | | |
| Malititol | 22.1228 | 21.6228 |
| Ace-K | 0.0350 | 0.0350 |
| Flavorant | 0.3430 | 0.3430 |
| Gum Arabic | 1.1678 | 1.1678 |
| Titanium Dioxide | 0.1780 | 0.1780 |
| Candelilla Wax | 0.0334 | 0.0334 |
| Sodium stearate** | 0.6667 | — |
| IMWITOR370 ®*** | — | 1.3333 |
| Sodium Oleate | — | — |
| Total | 100.0000 | 100.0000 |

*Aspartame, Ace K mixtures
**Sodium stearate/palmitate @ 50/50 is encapsulated in granular form which is 75% by weight sodium stearate.
***IMWITOR 370 ® in an encapsulated granular form which is 75% by weight IMWITOR 370 ®

Gum cores are prepared by the same conventional methods as in part A herein to form Samples 3-4. The molten gum base and the filler are added to the mixing kettle and mixing was commenced. The sugar alcohols, glycerin, flavors, and high intensity sweetener mixture, are added in portions with mixing to obtain a homogenous mixture. The mixture is then discharged from the mixing kettle and formed into cores by conventional techniques.

The cores are placed into a coating pan and broken into individual pieces as necessary. A sugarless solution containing 70% by weight of maltitol, as well as titanium dioxide, gum arabic and water is heated to between 70° and 80° C. The solution is sprayed onto the gum core pieces in layers and allowed to dry between sprays while the coating pan is continually rotating to ensure a smooth even coat of the gum cores.

The coating is built up to about 8% by weight of the final pellet weight. Ace-K is then added and then covered with another layer of the above-mentioned coating solution and then allowed to dry.

An encapsulated stain removing agent identified in Table 2 is prepared in the same manner as Part A herein.

After the high intensity sweetener layer is dried, the encapsulated stain removing agent and a flavorant are added in alternating layers until all of the respective materials are added with each layer being allowed to dry before the next layer is applied. The coating process is continued with the coating solution until the coat comprises 24% by weight of the final pellet weight.

The coating is then topped with a conventional finishing solution until a shell weight of 25% by weight is obtained.

The pellets are then polished in a polishing pan with candelilla wax in a conventional manner.

C. Coated Gums—Encapsulated Stain Removing Agent in Core

TABLE 3

| Ingredient | Sample 5 |
|---|---|
| Core Gum | |
| Gum Base | 26.2500 |
| Atomite (Filler) | 3.7500 |
| Sorbitol | 32.7743 |
| Mannitol | 7.5000 |
| Glycerin | 1.0000 |
| Flavorant | 2.8075 |
| High Intensity Sweetener* | 0.7875 |
| Sodium stearate** | 0.7507 |
| Coat | |
| Flavorant | 0.3430 |
| Ace-K | 0.0350 |
| Maltitol | 22.6228 |
| Gum Arabic | 1.1678 |
| Titanium Dioxide | 0.1780 |
| Candelilla Wax | 0.0334 |
| Total | 100.0000 |

*Aspartame, Ace K mixtures
**Sodium stearate/palmitate @ 50/50 is encapsulated in granules form which is 75% by weight sodium stearate.

Gum cores are prepared by the same conventional methods as the slab gum in part A herein with the encapsulated stain removing agent prepared as in part A being added last. The mixture is then discharged from the mixing kettle and formed into cores by conventional techniques.

The cores are placed into a coating pan and coated as in Part B herein with the exception that the application of an encapsulated stain removing agent-containing layer is eliminated from the process to form Sample 6 with the composition shown in Table 3.

E. Slab Gums

Samples 6 and 7 were prepared in the same manner as Sample 2 except that the average particle size of the encapsulated sodium stearate was less than 0.59 mm (Sample 6) and greater than 0.59 mm (Sample 7).

Example 2

Efficacy Tests of Gum Products

B. Chew Out Tests

Test I: 20 individuals were divided into 4 groups of 5 individuals each. Each group of individual in separate sessions chewed slabs of gum containing non-encapsulated sodium stearate as a control, the chewing gum composition of Sample 1, the chewing gum composition of Sample 6, and the chewing gum composition of Sample 7, respectively.

Each of the individuals chewed the 4 slabs of gum as described above for 20 minutes. The resulting bolus' were collected and analyzed to determine the amount of sodium stearate present in each slab before chewing (Table 4) and after chewing (Table 5).

TABLE 4

| Sample [a] | Individual | Sodium stearate (mg/piece) | | |
|---|---|---|---|---|
| | | Palmitate | Stearate | Total [b] |
| Control (non-encapsulated sodium stearate) | 1 | 6.01 | 3.98 | 9.99 |
| | 2 | 6.01 | 3.98 | 9.99 |
| | 3 | 6.17 | 4.00 | 10.17 |
| | 4 | 6.04 | 3.97 | 10.01 |
| | 5 | 6.13 | 4.05 | 10.18 |
| | | | | Average 10.07 |
| Sample 7 | 1 | 4.84 | 3.14 | 7.98 |
| | 2 | 4.64 | 3.06 | 7.70 |
| | 3 | 8.40 | 5.32 | 13.72 |
| | 4 | 6.69 | 4.42 | 11.11 |
| | 5 | 5.31 | 3.49 | 8.80 |
| | | | | Average 9.86 |
| Sample 6 | 1 | 6.80 | 4.39 | 11.19 |
| | 2 | 6.76 | 4.45 | 11.21 |
| | 3 | 6.66 | 4.35 | 11.01 |
| | 4 | 6.65 | 4.25 | 10.90 |
| | 5 | 7.14 | 4.66 | 11.80 |
| | | | | Average 11.22 |
| Sample 1 | 1 | 6.30 | 4.07 | 10.37 |
| | 2 | 6.53 | 4.21 | 10.74 |
| | 3 | 6.30 | 4.02 | 10.32 |
| | 4 | 6.15 | 4.06 | 10.21 |
| | 5 | 6.56 | 4.27 | 10.83 |
| | | | | Average 10.49 |

[a] separate analysis was performed for each sample
[b] Total sodium stearate is the sum of sodium palmitate and sodium stearate As shown in Table 4, each of the slabs of gum tested had about 10 mg of the stain-removing agent typically comprised of about 60% sodium palimitate and 40% sodium stearate. After chewing the amount of the stain-removing agent was determined and the results are set forth in Table 5.

TABLE 5

| Sample | Individual | Sodium stearate (mg/piece) | | |
|---|---|---|---|---|
| | | Palmitate | Stearate | Total [a] |
| Control | 1 | 5.75 | 3.49 | 9.24 |
| | 2 | 5.44 | 3.32 | 8.76 |
| | 3 | 5.74 | 3.44 | 9.18 |
| | 4 | 5.76 | 3.47 | 9.23 |
| | 5 | 5.63 | 3.38 | 9.01 |
| | | | | Average 9.08 |
| Sample 7 | 1 | 4.97 | 3.02 | 7.99 |
| | 2 | 5.65 | 3.16 | 8.81 |
| | 3 | 3.94 | 2.40 | 6.34 |
| | 4 | 5.60 | 3.36 | 8.96 |
| | 5 | 3.54 | 1.65 | 5.19 |
| | | | | Average 7.46 |
| Sample 6 | 1 | 5.40 | 3.14 | 8.54 |
| | 2 | 4.99 | 2.83 | 7.82 |
| | 3 | 5.25 | 3.00 | 8.25 |
| | 4 | 5.55 | 3.23 | 8.78 |
| | 5 | 4.97 | 2.75 | 7.72 |
| | | | | Average 8.22 |
| Sample 1 | 1 | 4.79 | 3.06 | 7.85 |
| | 2 | 5.28 | 3.13 | 8.41 |
| | 3 | 5.35 | 3.26 | 8.61 |
| | 4 | 5.45 | 3.33 | 8.78 |
| | 5 | 5.45 | 3.24 | 8.69 |
| | | | | Average 8.47 |

[a] Total sodium stearate is the sum of sodium palmitate and sodium stearate

The amount of the stain-removing agent released from the slab gum was determined and the results and shown in Table 6.

TABLE 6

| Sample | Sodium stearate (mg/piece) | | Sodium stearate |
|---|---|---|---|
| | Unchewed gum [a] | Chewed bolus [b] | % Release |
| Control | 10.07 | 9.08 | 10 |
| Sample 7 | 9.86 | 7.46 | 24 |
| Sample 6 | 11.22 | 8.22 | 27 |
| Sample 1 | 10.49 | 8.47 | 19 |

[a] The amount of sodium stearate in the unchewed gum is based on an average obtained from analyzing five slabs of unchewed gum.
[b] The amount of sodium stearate in the chewed bolus is based on an average obtained from analyzing five chewed bolus'.

As shown in Table 6, the gum compositions of the present invention including encapsulated stain-removing agent released from 19 to 27% of the stain-removing agent. This represented a 90 to 170% better release ratio than the gum composition containing the same stain removing agent in a non-encapsulated form. Especially good results were obtained when the average particle size of the encapsulated material was no more than about 0.5 mm.

Example 3

Preparation of Pressed Mint Products

Sample 8

A 2000 gram batch of a composition for forming a pressed mint product in accordance with the present invention is prepared in the following manner.

Sorbitol 97.5% by weight, 0.5% by weight of silicon dioxide, 0.3% by weight of a flavoring agent, and 0.7% of Aspartame are mixed for two minutes in a blender until a homogenous mixture is obtained. Encapsulated sodium stearate 1.0% by weight prepared in accordance with Example 1 is added to the mixture which is then blended for four minutes. The resulting mixture is then formed into individual pressed tablets in a conventional manner.

Samples 9

The procedure set forth in Sample 8 is repeated except that the amount of the encapsulated sodium stearate is increased from 1.0% to 10.0% with a corresponding reduction in the amount of sorbitol.

Sample 10 and Control

The procedure of Sample 8 was repeated for forming pressed tablet compositions containing the ingredients shown in Table 8 to form Sample 10.

TABLE 8

| INGREDIENT | SAMPLE 11 | CONTROL |
|---|---|---|
| Sorbitol Powder | 84.6220 | 99.6220 |
| Aspartame | 0.1000 | 0.1000 |
| Acesulfame Potassium Salt | 0.0500 | 0.0500 |
| Flavorant | 0.2280 | 0.2280 |
| Sodium Stearate | 15.0000 | — |

What is claimed is:

1. A method of producing a stain removing gum composition, comprising:
heating a gum base to soften the base;
mixing the softened gum base with an encapsulated particle consisting of a stain removing agent and a hydrophilic encapsulating material, wherein said at least one stain-removing agent is selected from the group consisting of medium and long chain fatty acid esters and salts, wherein the stain-removing agent is present in an amount from about 0.2 to 2.0% by weight based on the total weight of the gum composition, and where said encapsulated stain-removing agent has an average particle size of from 0.1 mm to 0.59 mm; and forming the mixture into gum pieces.

2. The method of claim 1, further comprising mixing the softened gum base with at least one of the group consisting of fillers, flavorants, sweeteners and softeners.

3. The method of claim 1, further comprising coating the gum pieces with a coating solution comprising the stain removing agent.

4. The method of claim 1, wherein the stain removing agent is present in an amount from about 0.4% to 2.0% by weight based on the total weight of the gum composition.

5. The method of claim 1, wherein the medium and long chain fatty acid esters and salts contain 8-24 carbon atoms.

6. The method of claim 1, wherein the medium and long chain fatty acid esters and salts contain 14-20 carbon atoms.

7. The method of claim 1, wherein the medium and long chain fatty acid esters and salts are selected from the group consisting of sodium salts of stearate, potassium salts of stearate, methyl esters of stearate, ethyl esters of stearate, sodium salts of palmitate, potassium salts of palmitate, methyl esters of palmitate, ethyl esters of palmitate, sodium oleate and mixtures thereof.

8. The method of claim 1, wherein the stain removing agent is present in the encapsulated stain removing agent in an amount from about 60 to 80% by weight based on the weight of the encapsulated stain removing agent.

9. The method of claim 1, wherein the stain removing agent is present in an amount from about 0.4 to 1.2% by weight based on the total weight of the gum composition.

10. The method of claim 1, wherein the hydrophilic encapsulating material is selected from the group consisting of carbohydrates, sugars, sugar alcohols, gums, cellulosic materials, proteins, wheat protein, water soluble polymers and mixtures thereof.

11. A method of preparing a stain removing gum composition, comprising:

providing a gum base composition;

preparing gum cores from the gum base composition; and coating the gum cores with a coating solution comprising an encapsulated particle consisting of a stain removing agent and a hydrophilic encapsulating material, wherein said at least one stain-removing agent is selected from the group consisting of medium and long chain fatty acid esters and salts, wherein the stain-removing agent is present in an amount from about 0.2 to 2.0% by weight based on the total weight of the gum composition, and where said encapsulated stain-removing agent has an average particle size of from 0.1 mm to 0.59 mm.

12. The method of claim 11, wherein the gum base composition further includes the stain removing agent.

13. The method of claim 11, wherein the gum base composition further includes at least one of the group consisting of fillers, flavorants, sweeteners and softeners.

14. The method of claim 11, wherein the medium and long chain fatty acid esters and salts contain 8-24 carbon atoms.

15. The method of claim 11, wherein the medium and long chain fatty acid esters and salts contain 14-20 carbon atoms.

16. The method of claim 11, wherein the medium and long chain fatty acid esters and salts are selected from the group consisting of sodium salts of stearate, potassium salts of stearate, methyl esters of stearate, ethyl esters of stearate, sodium salts of palmitate, potassium salts of palmitate, methyl esters of palmitate, ethyl esters of palmitate, sodium oleate and mixtures thereof.

17. The method of claim 11, wherein the stain removing agent is present in the encapsulated stain removing agent in an amount from about 60 to 80% by weight based on the weight of the encapsulated stain removing agent.

18. The method of claim 11, wherein the stain removing agent is present in an amount from about 0.4 to 1.2% by weight based on the total weight of the gum composition.

19. The method of claim 11, wherein the hydrophilic encapsulating material is selected from the group consisting of carbohydrates, sugars, sugar alcohols, gums, cellulosic materials, proteins, wheat protein, water soluble polymers and mixtures thereof.

* * * * *